United States Patent
Givens et al.

(10) Patent No.: US 6,502,040 B2
(45) Date of Patent: *Dec. 31, 2002

(54) METHOD FOR PRESENTING THROMBOSIS AND HEMOSTASIS ASSAY DATA

(75) Inventors: Thomas Givens, Rougemont; Paul Braun; Lisa Beck, both of Durham, all of NC (US)

(73) Assignee: bioMerieux, Inc., Durham, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/345,080

(22) Filed: Jun. 30, 1999

(65) Prior Publication Data

US 2002/0010553 A1 Jan. 24, 2002

Related U.S. Application Data

(63) Continuation-in-part of application No. 09/001,647, filed on Dec. 31, 1997.

(51) Int. Cl.[7] ............................................. G01N 21/00
(52) U.S. Cl. ............................ 702/22; 702/28; 702/30; 702/32
(58) Field of Search ...................... 702/22, 23, 27–32, 702/128, 131, 139, 179, 180, 183, FOR 115–FOR 119, FOR 17, FOR 171, FOR 131; 700/266, 268; 73/64.43; 436/66, 43, 47–50, 54, 55, 69, 174, 164, 171, 180, 805; 422/50, 61–67, 68.1, 73, 82.05; 382/133, 134, 156–159; 356/39, 40, 42; 706/924, 21, 20; 435/13; 377/10, 11; 703/6, 9, 11, 12

(56) References Cited

U.S. PATENT DOCUMENTS

| 3,307,392 A | 3/1967 | Owen et al. ................ 73/64.1 |
| 3,458,287 A | 7/1969 | Gross et al. ................. 23/230 |

(List continued on next page.)

FOREIGN PATENT DOCUMENTS

| DE | 2635081 | 2/1978 | .......... G01N/33/16 |
| DE | 3502 878 | 1/1985 | .......... C12Q/01/56 |
| EP | 0 115 459 | 8/1984 | .......... G01N/33/68 |
| EP | 0 434 377 | 6/1991 | .......... G01N/33/86 |
| EP | 0 525 273 | 2/1993 | .......... G01N/33/49 |

(List continued on next page.)

OTHER PUBLICATIONS

3 × 15 *Test Kit for Detection of Plasma Protein C Activity Using a Clotting End–Point*, Product # ACC–45, American Diagnostica Inc.,1–2 (Feb. 1989), 2 pages.

Artherotech, *VAP/CAD Lipoprotein Risk Assessment Tes and Sample of VAP Profile*, http://www.artherotech.com/risk assesment.html, 10 pages (No date).

Astion, et al., *Overtraining in neural networks that interpret clinical data*, Clin. Chem., 39(9):1998–2004 (1993). (No month).

(List continued on next page.)

*Primary Examiner*—Hal Wachsman
(74) *Attorney, Agent, or Firm*—Myers Bigel Sibley & Sajovec

(57) ABSTRACT

A method for presenting relationships between data from a thrombosis-hemostasis assay on an unknown sample and data from a purality of assays on known samples, which can be in the form of a topological feature map wherein spatial locations within the map correspond to intrinsic features of the known samples. The position of the unknown sample is superimposed on the positions of the known samples. An alternative presentation is showing the distance of each of a purality of predictor variables from an unknown sample to the mean values of a known population.

48 Claims, 7 Drawing Sheets

U.S. PATENT DOCUMENTS

| | | | |
|---|---|---|---|
| 3,658,480 A | 4/1972 | Kane et al. | 23/230 B |
| 4,040,788 A | 8/1977 | Simons et al. | 436/34 |
| 4,047,890 A | 9/1977 | Eichelberger et al. | 23/230 B |
| 4,199,748 A | 4/1980 | Bacus | 340/146.3 CA |
| 4,217,107 A | 8/1980 | Saito et al. | 23/230 B |
| 4,279,616 A | 7/1981 | Saito et al. | 23/230 B |
| 4,289,498 A | 9/1981 | Baughman et al. | 23/230 B |
| 4,766,083 A | 8/1988 | Miyashita et al. | 436/517 |
| 4,782,014 A | 11/1988 | Serban et al. | 435/7 |
| 4,902,630 A | 2/1990 | Bennett et al. | 436/546 |
| 4,965,725 A | 10/1990 | Rutenberg | 364/413.1 |
| 4,998,535 A | 3/1991 | Selker et al. | 128/696 |
| 5,003,065 A | 3/1991 | Merritt et al. | 540/469 |
| 5,055,412 A | 10/1991 | Proksch | 436/69 |
| 5,156,974 A | 10/1992 | Grossman et al. | 436/69 |
| 5,169,786 A | 12/1992 | Carroll et al. | 436/69 |
| 5,218,529 A | 6/1993 | Meyer et al. | 364/413.01 |
| 5,221,628 A | 6/1993 | Anderson et al. | 436/507 |
| 5,358,852 A | 10/1994 | Wu | 435/7.94 |
| 5,388,164 A | 2/1995 | Yonekawa et al. | 382/6 |
| 5,473,551 A | 12/1995 | Sato et al. | 364/496 |
| 5,473,732 A | 12/1995 | Chang | 395/77 |
| 5,500,345 A | 3/1996 | Soe et al. | 435/7.1 |
| 5,525,477 A | 6/1996 | Hassouna | 436/69 |
| 5,526,111 A | 6/1996 | Collins et al. | 73/64.43 |
| 5,553,616 A | 9/1996 | Ham et al. | 128/633 |
| 5,563,983 A | 10/1996 | Nozaki et al. | 395/23 |
| 5,567,596 A | 10/1996 | Diamond et al. | 435/13 |
| 5,591,403 A | 1/1997 | Gavin et al. | 422/73 |
| 5,593,897 A | 1/1997 | Potempa et al. | 436/507 |
| 5,646,046 A | 7/1997 | Fischer et al. | 436/49 |
| 5,670,329 A | 9/1997 | Oberhardt | 435/13 |
| 5,705,395 A | 1/1998 | Griffin et al. | 436/69 |
| 5,708,591 A | 1/1998 | Givens et al. | 364/497 |
| 5,715,821 A * | 2/1998 | Faupel | 706/924 |
| 5,716,795 A | 2/1998 | Matschiner | 435/13 |
| 5,834,223 A * | 11/1998 | Griffin et al. | 435/13 |
| 5,856,114 A * | 1/1999 | Mann et al. | 436/69 |
| 5,862,304 A | 1/1999 | Ravdin et al. | 395/22 |
| 5,981,285 A | 11/1999 | Carroll et al. | 702/23 |
| 6,010,911 A | 1/2000 | Baugh et al. | 422/73 |
| 6,040,147 A | 3/2000 | Ridker et al. | 435/7.24 |
| 6,101,449 A | 8/2000 | Givens et al. | 702/22 |
| 6,269,313 B1 | 7/2001 | Givens et al. | 702/22 |

FOREIGN PATENT DOCUMENTS

| | | | |
|---|---|---|---|
| EP | 818 680 | 1/1998 | G01N/33/546 |
| EP | 841 566 | 5/1998 | G01N/33/96 |
| FR | 2364 453 | 9/1976 | G01N/33/16 |
| GB | 2005014 | 4/1979 | G01N/33/16 |
| JP | 59-203959 | 11/1984 | G01N/33/86 |
| JP | 60-114768 | 6/1985 | G01N/35/02 |
| JP | 61-272655 | 12/1986 | G01N/33/49 |
| JP | 5-180835 | 12/1991 | G01N/33/53 |
| JP | 6-027115 | 7/1992 | G01N/33/86 |
| JP | 4-254760 | 9/1992 | G01N/33/53 |
| JP | 6-249855 | 9/1994 | G01N/33/86 |
| JP | 10-104239 | 9/1996 | G01N/33/86 |
| RU | 2012877 | 4/1991 | G01N/33/48 |
| RU | 2061953 | 6/1996 | G01N/33/86 |
| RU | 2070327 | 12/1996 | G01N/33/50 |
| SU | 590665 | 2/1976 | G01N/33/16 |
| SU | 1076086 | 2/1984 | A61B/5/14 |
| SU | 1691741 | 8/1989 | G01N/33/48 |
| SU | 1777089 | 6/1990 | G01N/33/86 |
| WO | WO 86/06840 | 11/1986 | G01N/33/86 |
| WO | WO 89/09628 | 10/1989 | |
| WO | WO 91/00872 | 1/1991 | C07K/15/28 |
| WO | WO 91/01383 | 2/1991 | C12Q/1/56 |
| WO | WO 91/01497 | 2/1991 | G01N/31/00 |
| WO | WO 91/02812 | 3/1991 | C12Q/1/56 |
| WO | WO 91/05874 | 5/1991 | C12Q/1/00 |
| WO | WO 91/08460 | 6/1991 | G01N/21/00 |
| WO | WO 91/16453 | 10/1991 | C12Q/1/56 |
| WO | WO 93/07491 | 4/1993 | G01N/33/68 |
| WO | WO 93/09438 | 5/1993 | G01N/33/68 |
| WO | WO 93/24530 | 12/1993 | C07K/15/06 |
| WO | WO 94/07145 | 3/1994 | G01N/33/86 |
| WO | WO 94/11714 | 5/1994 | G01J/3/02 |
| WO | WO 94/16095 | 7/1994 | C12Q/1/00 |
| WO | WO 95/05590 | 2/1995 | G01N/1/28 |
| WO | WO 95/08121 | 3/1995 | G01N/33/86 |
| WO | WO 96/42018 | 9/1995 | G01N/33/86 |
| WO | WO 95/30154 | 11/1995 | G01N/33/86 |
| WO | WO 96/06624 | 3/1996 | A61K/35/16 |
| WO | WO 96/14581 | 5/1996 | G01N/33/86 |
| WO | WO 96/21740 | 7/1996 | C12Q/1/56 |
| WO | WO 96/41291 | 12/1996 | G06F/19/00 |
| WO | WO 97/04317 | 2/1997 | G01N/33/68 |
| WO | WO 97/20066 | 6/1997 | C12Q/1/56 |
| WO | WO 97/34698 | 9/1997 | B01L/3/00 |
| WO | WO 98/09628 | 3/1998 | A61K/31/495 |
| WO | WO 99/34208 | 7/1999 | |
| WO | WO 99/47699 | 9/1999 | |

OTHER PUBLICATIONS

Astion, et al., *The application of backpropagation neural networks to problems in pathology and laboratory medicine*, Arch. Pathol. Lab. Med., 116:995–1001 (Oct. 1992).

Baum and Haussler, *What size net gives valid generalization?*, Neural Computation, pp. 81–89 (Jan. 1989).

Baumann et al., *Computerized analysis of the in vitro activation of the plasmatic clotting system*, Haemostasis, 19:309–321 (1989). (No month).

Bluestein and Archer, *The sensitivity, specificity and predictive value of diagnostic information: a guide for clinicians*, Nurse Practitioner, 16(7):39–45 (Jul. 1991).

Boone et al., *Neural networks in radiologic diagnosis*, Investigative Radiology, 25(9):1012–1023 (Sep. 1990).

Brandt, et al., *Effect of lupus anticoagulants on the activated partial thromboplastin time. Results of the College of American Pathologists survey program*, Arch.Pathol.Lab Med., 115:109–114 (Feb. 1991).

Braun et al., *Examination of prothrombin time (PT) and activated partial thromboplastin time (APTT) optical clot profiles using an automated thromobosis–hemostasis*, Coagulation Methods Instrumentation and Quality Control, p. 1236, Abstract #1286 (1995). (No month).

Braun, et al., *Properties of optical data from activated partial thromboplastin time and prothrombin time assays*, Thromb.Haemost., 78:1079–1087 (1997).

Cabana, et al., *Effects of the acute phase response on the concentration and density distribution of plasma lipids and apolipoproteins*, J.Lipid Res., 30:39–49 (1989).

Cabana, et al., *Inflammation–induced changes in rabbit CRP and plasma lipoproteins*, J.Immunol., 130(4):1736–1742 (Apr. 1983).

Cabana, et al., *Interaction of very low density lipoproteins (VLDL) with rabbit C–reactive protein*, J.Immunol., 128(5):2342–2348 (May 1982).

Canivet, et al., *Postoperative changes in lipid profile: their relations with inflammatory markers and endocrine mediators*, Acta Anaesthesiol.Belg., 40(4):263–268 (1989) (No month).

Carrol, et al., *Ortho Educational Monograph, The Clot Signature and New Aspects in Coagulation Testing*, Ortho Diagnostic Systems, Inc., pp. 1–20 (1989). (No month).

Christner and Mortensen, *Specificity of the binding interaction between human serum amyloid P–component and immobilized human C–reactive protein*, J.Biol.Chem., 269(13):9760–9766 (Apr. 1994).

Dassen, et al., *Self–learning neural networks in electrocardiography*, J.Electrocardiol., 23 Suppl:200–202 (1990). (No month).

de Beer, et al., *Low density lipoprotein and very low density lipoprotein are selectively bound by aggregated C–reactive protein*, J.Exp.Med., 156:230–242 (Jul. 1982).

Dennis et al., *Utility of prothrombin time waveform analysis in the routine clinical setting, Abstract Instruction and Submission Form*, (Sep. 1999), 1 page.

Downey et al., *The robustness and reproducibility of APTT waveform analysis in relation to reagent and batch variation*, abstract only (No date).

Downey et al., *Transmittance waveforms –adjunctive information from automated coagulometers*, Int.J.Hematol., 64 Suppl:S160, Abstract #619, (Aug. 1996), 1 page.

Downey, et al., *Novel and diagnostically applicable information from optical waveform analysis of blood coagulation in disseminated intravascular coagulation*, Br.J.Haematol., 98:68–73 (1997), pp. 1–6 (No month).

Furlong, et al., *Neural network analysis of serial cardiac enzyme data. A clinical application of artificial machine intelligence*, Am.J.Clin.Pathol., 96(1):134–141 (Jul. 1991).

Gewurz, et al., *C–reactive protein and the acute phase response*, Adv.Intern.Med., 27:345–372 (1982).

Givens and Braun, *Classification of factor deficiencies from coagulation assays using neural networks*, Int.J.Med.Inf., 46:129–143 (1997). (No month).

Givens et al., *Interpretation of clot formation parameters from APTT and PT assays using neural networks*, Clin.Chem., 42(6):S192, Abstract #399 (1996), 1 page. (No month).

Givens, et al., *Predicting the presence of plasma heparin using neural networks to analyze coagulation screening assay optical profiles*, Comput.Biol.Med., 26(6):463–476 (1996) (No month).

Givens, T.B., *Clot signatures*, Clin.Hemostasis Rev., pp. 11–12 (Aug. 1997).

Harris et al., *Reactivity of serum amyloid P component with C–reactive protein and IgM*, Clin.Res., 37, Abstract #614A (1989). (No month).

Heuck and Baumann, *Kinetic analysis of the clotting system in the presence of heparin and depolymerized heparin*, Haemostasis, 21:10–18 (1991). (No month).

Hoffman and Callahan, *The Coag–A–Mate RA4 Fibrinogen Assay*, Interface (Organon Teknika), pp. 3–7 (1990) (No month).

Hulman and Fuller, *Comparison of flat agglutination slide test and latex test for C–reactive protein*, Clin.Chim.Acta, 165:89–93 (May 29, 1987).

Hulman, et al., *Agglutination of intralipid by sera of acutely ill patients*, Lancet, 2:1426–1427 (Dec. 1982).

Hulman, G., *The pathogenesis of fat embolism*, J.Pathol., 176:3–9 (1995). (No month).

Husebekk, et al., *High–density lipoprotein has different binding capacity for different apoproteins. The amyloidogenic apoproteins are easier to displace from high––density lipoprotein*, Scand.J.Immunol., 28:653–658 (1988). (No month).

*Koagulab 16–S Plus Graphics, Koagulab 32–S Coagulation System, Graphics Binder*, 2,3,5,6,8–12, 14–17,19–21,23. (No date).

Khanin and Semenov, *A mathematical model of the kinetics of blood coagulation*, J.Theor.Biol., 136:127–134 (Jan. 1989).

Lagrand, et al., *C–reactive protein as a cardiovascular risk factor: more than an epiphenomenon?*, Circulation, 100:96–102 (Jul. 1999).

Lindh, et al., *Agglutinate formation in serum samples mixed with intravenous fat emulsions*, Crit Care Med., 13(3):151–154 (Mar. 1985).

Malle, et al., *Serum amyloid A (SAA): an acute phase protein and apolipoprotein*, Atherosclerosis, 102:131–141 (1993). (No month).

McCarty, M., *Historical perspective on C–reactive protein*, Ann.N.Y.Acad.Sci., 389:1–10 (1982) (No month).

McDonald, et al., *A monoclonal antibody sandwich immunoassay for serum amyloid A (SAA) protein*, J.Immunol.Methods, 144:149–155 (Nov. 22, 1991).

*Package insert for Ortho Brain Thromboplastic Reagent*, Ortho Diagnostic System, Inc., pp. 1–7 (Oct. 1985).

Pattichis, et al., *Efficient training of neural network models in classification of electromyographic data*, Med.Biol.Eng Comput., 33(3):499–503 (May 1995).

Pepys, et al., *C–reactive protein: binding to lipids and lipoproteins*, Int.Rev.Exp.Pathol., 27:83–111 (1985). (No month).

Pohl, et al., *The quick machine—a mathematical model for the extrinsic activation of coagulation*, Haemostasis, 24:325–337 (1994). (No month).

Richter, et al., *The fat emulsion agglutination test: a reliable and cost effective alternative to the latex agglutination test for rapid bedside CRP measurement*, Clin.Chim.Acta, 261:141–148 (May 1997).

Robin et al., *Prognostic value of waveform analysis in the intensive care setting*, Intensive Care Med., 25(Suppl 1):S63 (1999). (No month).

Rowe, et al., *Agglutination of intravenous lipid emulsion ('Intralipid') and plasma lipoproteins by C–reactive protein*, Clin.Exp.Immunol., 66:241–247 (1986). (No month).

Rowe, et al., *Circulatin human C–reactive protein binds very low density lipoproteins*, Clin.Exp.Immunol., 58:237–244 (1984). (No month).

Rowe, et al., *In vivo turnover studies of C–reactive protein and lipoproteins in the rabbit*, Clin.Exp.Immunol., 58:245–252 (1984). (No month).

Rowe, et al., *Rabbit and rat C–reactive proteins bind apolipoprotein B–containing lipoproteins*, J.Exp.Med., 159:604–616 (Feb. 1984).

Sabbatini, R.M.E., *Neural networks for classification and pattern recognition of biological samples*, Conf.of the Engineering in Medicine and Biology Society (IEEE, New York, U.S.) 15:265–266 (Oct. 1983).

Sammalkorpi, et al., *Lipoproteins and acute phase response during acute infection. Interrelationships between C–reactive and serum amyloid–A protein and lipoproteins*, Ann.Med., 22:397–401 (1990). (No month).

Schwalbe, et al., *Association of rat C–reactive protein and other pentraxins with rat lipoproteins containing apolipoproteins E and A1*, Biochemistry, 34(33):10432–10439 (Aug. 1995).

Schweiger, et al., *Evaluation of laboratory data by conventional statistics and by three types of neural networks*, Clin.Chem., 39:(9):1966–1971 (1993). (No month).

Simmons, A. *Ehanol–gel solubitlity test*, In: Technical Hematology, 3rd Edition, J.B. Lippincott Company, Philadelphia, PA, pp. 334–335 (1980). (No month).

Stewart, et al., *Sensitive and rapid measurement of C–reactive protein (CRP) by lipid agglutination*, J.Clin.Pathol., 40:585–588 (1987). (No month).

Swanson, et al., *Human serum amyloid P–component (SAP) selectively binds to immobilized or bound forms of C–reactive protein (CRP)*, Biochim.Biophys.Acta, 1160:309–316 (Dec. 28, 1992).

Sweeney et al., *Abnormal clot signatures in hereditary bleeding disorders*, Blood, 74 Suppl 1(7):395, Abstract #1509 (Nov. 1989), 1 page.

Sweeney et al., *Abnormal clot signatures in hereditary bleeding disorders*, The American Society of Hematology Abstract Reproduction Form (1989), 1 page. (No month).

Sweeney et al., *Kinetic clot parameters in gynecological tumors*, Blood, 76 Suppl 1(10):439a, Abstract #1745–(Nov. 1990), 1 page.

Swets, J. A., *Measuring the accuracy of diagnostic systems*, Science, 240:1285–1293 (Jun. 1988).

Talstad, I., *Which coagulation factors interfere with the one–stage prothrombin time?*, Haemostasis, 23:19–25 (1993). (No month).

Toh and Downey, *A previously unrecognized mechanism that is calcium–dependent and thrombin–independent characterizes the pre–DIC state*, The American Society of Hematology, 1999 Submission Form, Abstract #450426 (1999), 1 page. (No month).

Toh and Downey, *The mechanism underlying the atypical clot waveform profile of DIC is thrombin–independent but calcium–dependent*, European Haematology Association, Abstract Form (Jun. 2000), 1 page.

Toh et al., *APTT Waveform analysis: predicting mortality in the critical care setting using the light transmittance level at 18 seconds*, XVII Congress International Society for Thrombosis & Haemostasis, Abstract Submission Form, (Aug. 1999), 1 page.

Toh et al., *Characterization of the novel calcium–activation, thrombin suppression assay (CaTs) in the DIC of sepsis*, abstract only. (No date).

Toh et al., *Impending clinical decompensation is characterized by the detection of a novel calcium–dependent and thrombin–independent pathway*, 5th World Congress on Trauma, Shock, Inflammation and Sepsis —Pathophysiology, Immune Consequences and Therapy, Abstract Submission Form, (Feb. 2000), 1 page.

Toh et al., *Prospective detection of pre–disseminated intravascular coagulation (DIC) in a sepsis cohort by waveform analysis*, XVII Congress International Society for Thrombosis & Haemostasis, Abstract Submission Form, (Aug. 1999), 1 page.

Toh et al., *Waveform analysis of the prothrombin time (PT) assay also shows characteristic changes in disseminated intravascular coagulation*, XVII Congress International Society for Thrombosis & Haemostasis, Abstract Submission Form, (Aug. 1999), 1 page.

Toh, C.H., *Disseminated intravascular coagulation (DIC): Old problem, new hope*, Clin.Hemostasis Rev., p. 18 (Jan. 1998), 1 page only.

Triplett, et al., *Graphic monitoring of coagulation assays*, American Clinical Laboratory, pp. 1–5 (Apr. 1989).

Wilkins, et al., *Rapid automated enzyme immunoassay of serum amyloid A*, Clin.Chem., 40(7):1284–1290 (1994). (No month).

Zweig and Campbell, *Receiver–operating characteristic (ROC) plots: a fundamental evaluation tool in clinical medicine*, Clin.Chem., 39(4):561–577 (1993). (No month).

*Ortho Factor VIII: C Deficient Plasma*, Ortho Diagnostic Systems, Inc., pp. 1–2 (Sep. 1988).

C. Downey, et al. Br. J. Haematol., 136: 18854 (1997). (No month).

Preciado–Pratt et al. *Serum Amyloid A Complexed with Extracellular Matrix Induces the Secretion of Tumor Necrosis Factor–alpha by Human T–lymphocytes*, Letters in Peptide Science, vol. 5, (1998), No. 5–6, pp. 349–355. (No month).

Eitoku et al., "Studies on the Serum Amyloid A (SAA): Part 2 Latex Agglutination Nephelometric Immunoassay System for Quantitation of SAA in Human Serum and its Clinical Values," *Physico Chem. Biol.*, 37:19–23 (Feb. 1993). (No translation).

Rybarska et al. "The Detective of Specific Acute Phase Serum Protein Complexes and Immune Complexes by Congo Red Binding," *Journal of Physiology and Pharmacology*, 1995, vol. 46, (2), pp. 221–31. (No month).

Maury, C.P.J. "Clinical Usefulness of Serum Amyloid A and C–reactive Protein Measurements in Inflammatory Disorders a Comparative Study," *Marker Proteins in Inflammation Proceedings*, vol. 3, Symposium, Lyon, France, Jun. 1985 pp. 153–156.

Baumann et al., "Stimulation of the extrinsic pathway of the plasmatic clotting system," *Haemostasis*, 21:329–337 (1991). (No month).

Zuckerman et al. "Comparison of thrombelastography with common coagulation tests," *Thromb Haemostas*, 46: 752–756 (1981). (No month).

\* cited by examiner

FIG. 2

Predictor Variables

| Predictor Variable | Description |
|---|---|
| $pv_{j1} = \left(\dfrac{dT}{dt}\right)_{min}$ | minimum of the first derivative |
| $pv_{j2} = t$ at $\left(\dfrac{dT}{dt}\right)_{min}$ | time index of the minimum of the first derivative |
| $pv_{j3} = \left(\dfrac{d^2T}{dt^2}\right)_{min}$ | minimum of the second derivative |
| $pv_{j4} = t$ at $\left(\dfrac{d^2T}{dt^2}\right)_{min}$ | time index of the minimum of the second derivative |
| $pv_{j5} = \left(\dfrac{d^2T}{dt^2}\right)_{max}$ | maximum of the second derivative |
| $pv_{j6} = t$ at $\left(\dfrac{d^2T}{dt^2}\right)_{max}$ | time index of the maximum of the second derivative |
| $pv_{j7} = T_{t_o} - T_{t_n}$ | overall change in transmittance during the reaction |
| $pv_{j8} = \dfrac{(T_{pv_{j2}} - T_{t_o})}{pv_{j2} \, t_n}$ | pre-coagulation slope |
| $pv_{j9} = \dfrac{(T_{t_{max}} - T_{pv_{j5}})}{(t_{max} \, pv_{j5})_{t_n}}$ | pre-coagulation slope |

METHOD FOR PRESENTING THROMBOSIS AND HEMOSTASIS ASSAY DATA

This application is a continuation-in-part of U.S. patent application Ser. No. 09/001,647 to Braun et al., filed Dec. 31, 1997, now U.S. Pat. No. 6,321,164 the subject matter of which is incorporated by reference. This application also relates to U.S. Pat. No. 5,646,046 to Fischer et al, the subject matter of which is incorporated herein by reference. This application is further related to the following publications, the subject matter of each also being incorporated herein by reference:

1. B. Pohl, C. Beringer, M. Bomhard, F. Keller, The quick machine—a mathematical model for the extrinsic activation of coagulation, *Haemostasis*, 24, 325–337 (1994).
2. I. Talstad, Which coagulation factors interfere with the one-stage prothrombin time?, *Haemostasis*, 23, 19–25 (1993).
3. P. Baumann, T. Jurgensen, C. Heuck, Computerized analysis of the in vitro activation of the plasmatic clotting system, *Haemostasis*, 19 309–321 (1989).
4. C. Heuck, P. Baumann, Kinetic analysis of the clotting system in the presence of heparin and depolymerized heparin, *Haemostasis*, 21, 10–18 (1991).
5. T. Kohonen, The Self-organizing map, *Proc. IEEE*, 78, 1464–1480 (1990).
6. M. Zweig and G. Campbell, Receiver-operating characteristic (ROC) plots: a fundamental evaluation tool in clinical medicine, *Clinical Chemistry*, 39, 561–577 (1993).

BACKGROUND OF THE INVENTION

Thrombosis and hemostasis testing involves the in vitro study of the ability of blood to form clots and to dissolve clots in vivo. A variety of coagulation (hemostasis) assays are used to identify congenital or acquired disorders of the coagulation system and to monitor the administration of therapeutic drugs.

Two assays, the, prothrombin time (PT) and activated partial thromboplastin time (APTT), are widely used to screen for abnormalities in the coagulation system, although several other screening assays can be used, e.g. protein C, fibrinogen, protein S and/or thrombin time. These assays usually measure clot time, the time required to initiate clot formation following the addition of a coagulation activating agent to blood or plasma. (Some variations of the PT also use the amplitude of the change in optical signal to estimate fibrinogen concentration). Automated methods determine clot time based on changes in electromechanical properties, clot elasticity, light scattering, fibrin adhesion, impedance or other properties. For light scattering methods, data is gathered that represents the transmission of light through the specimen as a function of time (one example of an optical time-dependent measurement profile).

Blood coagulation is affected by administration of drugs, in addition to the vast array of internal factors and proteins that normally influence clot formation. For example, heparin is a widely-used therapeutic drug that is used to prevent thrombosis following surgery or under other conditions, or is used to combat existing thrombosis. The administration of heparin is typically monitored using the APTT assay, which gives a prolonged clot time in the presence of heparin. Clot times for PT assays are affected to a much smaller degree. Since a number of plasma abnormalities or therapeutic conditions may cause a prolonged APTT result, one or several additional tests are needed to isolate the exact source of the abnormality. The ability to discriminate between these effectors from screening assay results may be clinically significant.

The present invention was conceived of and developed for presenting the relationships between an unknown sample and samples from known populations. The invention is intended to facilitate analysis of information embedded in the data from coagulation assays that is not included in the conventional data analysis for these assays. The additional information can help discriminate between underlying conditions and aid in the identification of otherwise undetected conditions.

SUMMARY OF THE INVENTION

The present invention is directed to a method for presenting the relationship between data from an assay relating to thrombosis-hemostasis on an unknown sample, and data from a plurality of assays relating to thrombosis-hemostasis from known sample populations, including:

(a) providing data from at least one time-dependent measurement profile for each of a plurality of known blood samples (the blood samples can be whole blood, or a portion thereof such as plasma);

(b) measuring a property over time to derive at least one time-dependent measurement for an unknown blood sample;

(c) transforming data from steps (a) and (b) to a plurality of predictor variables which sufficiently capture the information content of the time-dependent measurements from both the known blood samples and unknown blood sample;

(d) presenting the data from said unknown blood sample time-dependent measurement profile relative to the data from said known blood sample time-dependent measurement profiles using the presentation method of either steps (e), (f), and (g), or steps (h) and (i);

(e) creating a topological feature map of the sets of predictor variables from step (c) of the known samples in step (a) whose spatial locations within the map correspond to intrinsic features of the sets of predictor variables;

(f) determining the position on the map of the unknown sample corresponding to its set of predictor variables;

(g) presenting the data from said unknown blood sample time-dependent measurement profile relative to the data from said known blood sample time-dependent measurement profiles;

(h) computing the standard deviation for each predictor variable in step (c) of the known samples in step (a);

(i) determining the z-score of the unknown sample in (b) for each predictor variable, and determining if one or more of the z-scores for the unknown sample is greater than a predetermined limit, signifying that the unknown sample is different from the known population represented by the model.

BRIEF DESCRIPTION OF THE DRAWINGS

FIG. 2 is a chart listing examples of predictor variables for use in the present invention;

Figure 4:
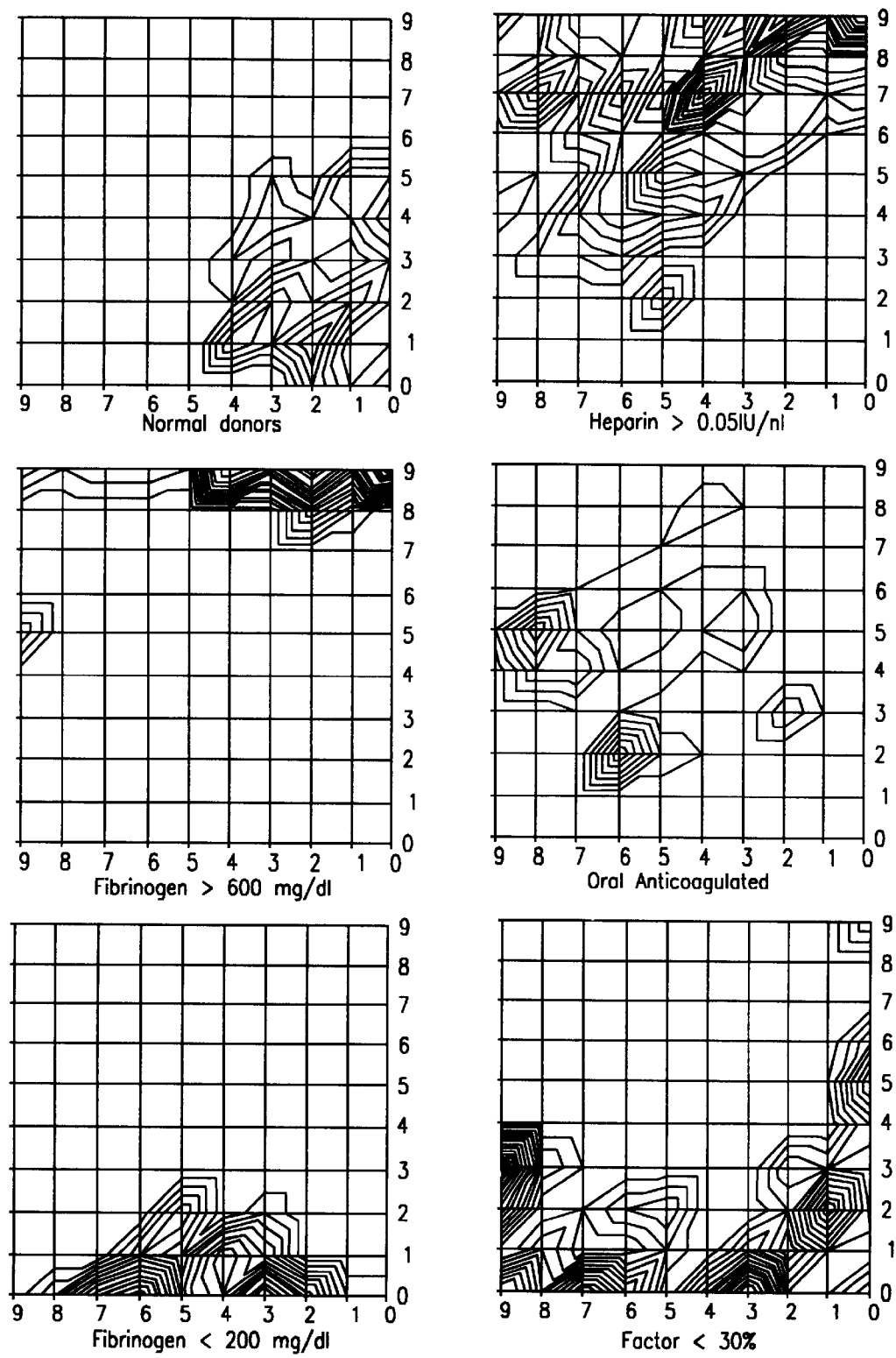

(1) normal donors, (2) heparinized samples, (3) specimens with elevated fibrinogen, (4) specimens with low fibrinogen, (5) specimens from patients receiving oral anticoagulants, and (6) specimens with low factor concentration (Factor II,V,VII,VIII,IX,X,XI, or XII);

FIG. 4 shows SOM contour plots derived from PT optical data for six specimen categories (1) normal donors, (2) heparinized samples, (3) specimens with elevated fibrinogen, (4) specimens with low fibrinogen, (5) specimens from patients receiving oral anticoagulants, and (6) specimens with low factor concentration (Factor II,V,VII, VIII,IX,X,XI, or XII)

Figure 5:
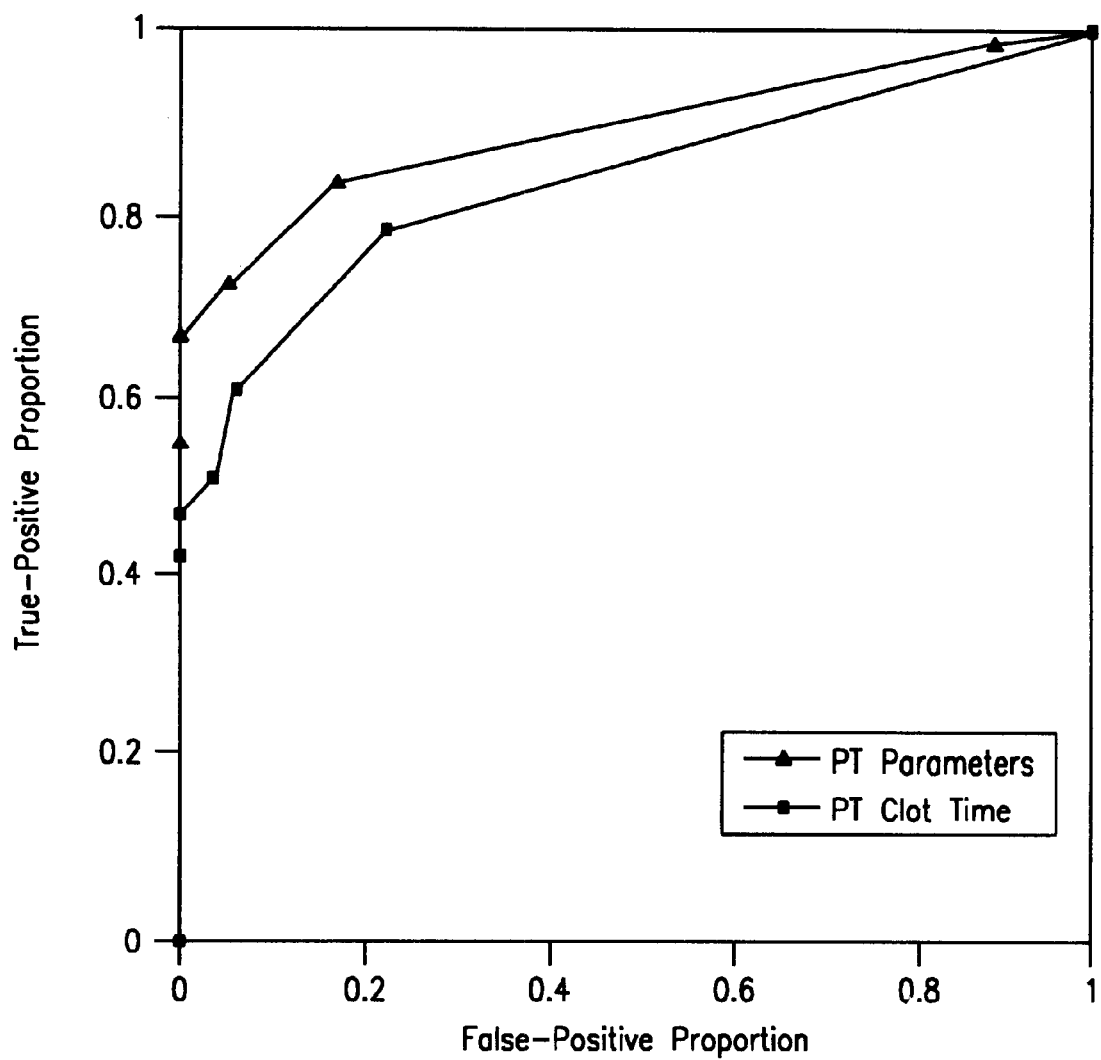

FIG. 5 is a receiver-operator characteristic (ROC) plot for identification of "normal" (negative) and "abnormal" (positive) samples using a PT clot time alone and using all predictor variables (if one or more predictor variables is outside x SD's of the normal range, than the sample is considered "positive", where x is 1sd, 2d, 3sd, etc).

Figure 6:
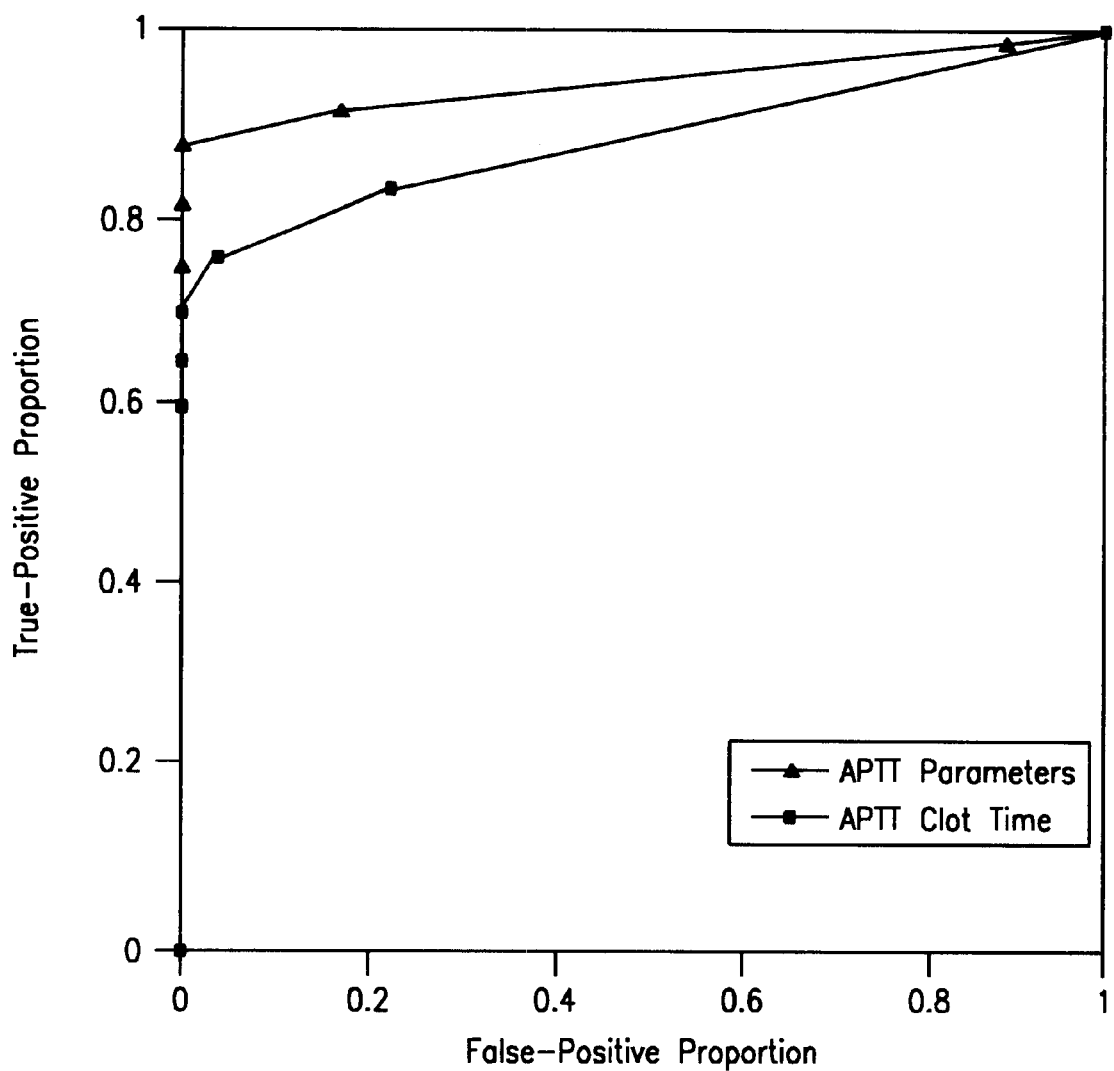

FIG. 6 is an ROC plot for identification of "normal" (negative) and "abnormal" (positive) samples using an APTT clot time alone and using all predictor variables (if one or more predictor variables is outside x SD's of the normal range, than the sample is considered "positive", where x is 1sd, 2sd, 3sd, etc).

Figure 7:
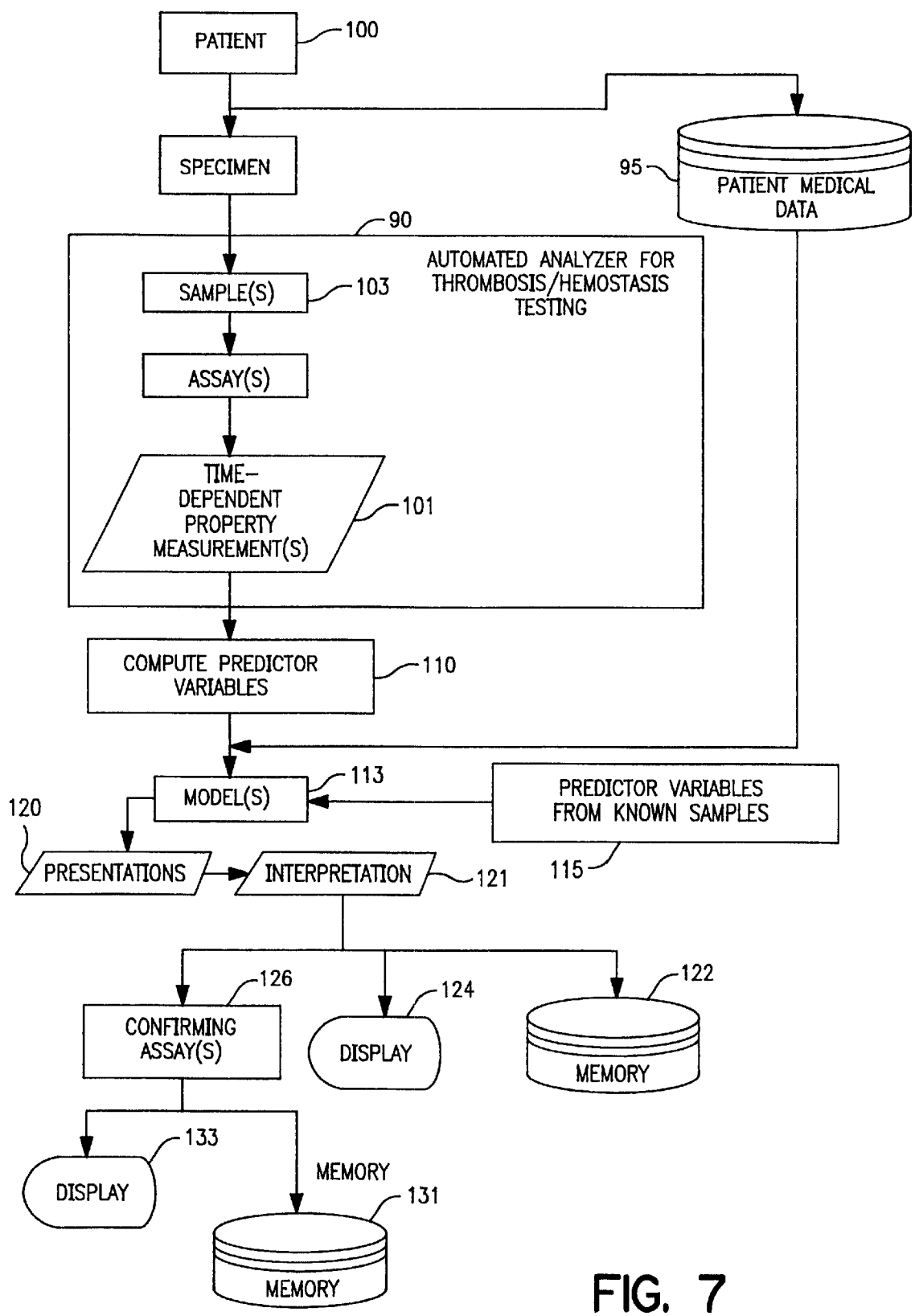

FIG. 7 is a diagram illustrating key aspects of the present invention.

DESCRIPTION OF THE PREFERRED EMBODIMENTS

In the present invention, both a method and apparatus are provided for presenting data from an unknown specimen as a function of known specimen population or populations. As can be seen in FIG. 7, one or more time-dependent measurements (101) are performed on an unknown sample (103). The term "time-dependent measurement" is referred to herein to include (but is not limited to) measurements derived from assays (e.g. PT, APTT, fibrinogen, protein C, protein S, TT, and factor coagulation-based assays). The term "unknown sample" refers to a sample, such as one from a medical patient (100), where a congenital or acquired imbalance or therapeutic condition associated with thrombosis/hemostasis is not known (or, if suspected, has not been confirmed). In the present invention, a coagulation property is measured over time so as to derive a time-dependent measurement profile. In a preferred embodiment, the time-dependent measurement is an optical measurement for deriving an optical profile corresponding to changes in light scattering and/or light absorption. For example, a PT profile, a fibrinogen profile, a TT profile, an APTT profile and/or variations thereof can be provided where, an unknown sample is analyzed for clot formation based on light transmittance over time through the unknown sample. In another preferred embodiment, optical measurements at two (or more) wavelengths can be taken over time so as to derive multiple optical profiles. In another preferred embodiment, two (or more) optical profiles are provided, such as both a PT profile and an APTT profile.

In one embodiment of the present invention, the method is performed on an automated analyzer (90). The time-dependent measurement profile, such as an optical data profile, can be provided automatically by the automated analyzer, where the unknown sample is automatically removed by an automated probe from a sample container to a test well, one or more reagents are automatically added to the test well so as to initiate the property changes within the sample which are monitored, and recorded by the analyzer.

Figure 1:
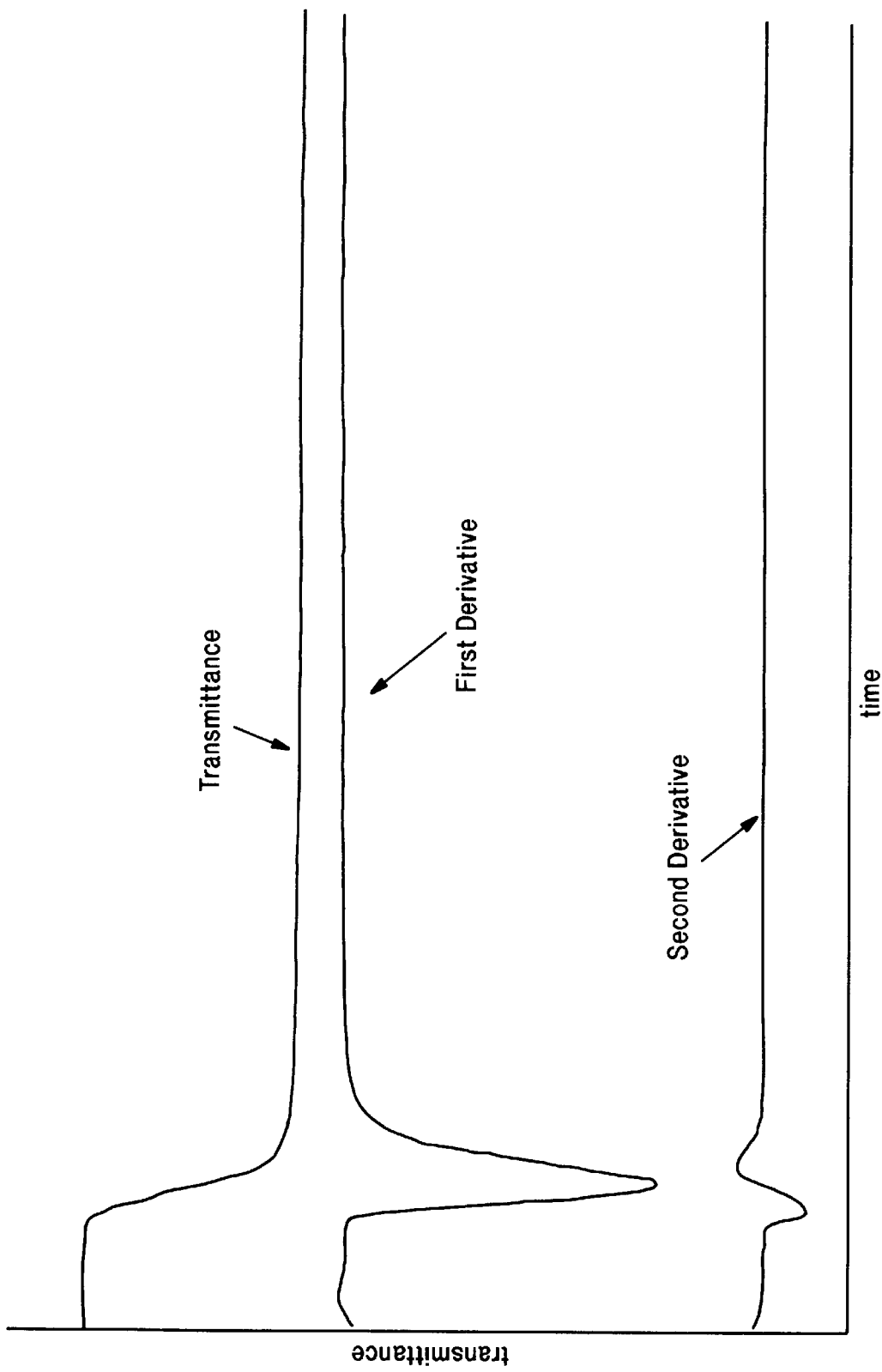
FIG. 1 is an optical profile with first and second derivatives of a normal clotting sample.

After the time-dependent measurement profiles are provided, a set of predictor variables are defined (110) which sufficiently define the data of the time-dependent profiles. In a preferred embodiment, one or more of (at least) nine predictor variables were used (though more preferably a plurality of such variables are used—and in some cases three or more of the at least nine variables are used). In this approach, the optical data for a PT or APTT assay was divided into three segments (a pre-coagulation segment, a coagulation segment and a post-coagulation segment) using divisions based on the minimum and maximum value of the second derivative for changes in optical signal with respect to time. Parameters included: 1) the times at which the onset, midpoint and end of the coagulation phase occur; 2) mean slopes for the pre-coagulation phase and the post-coagulation phase and the slope at the mid-point of coagulation; 3) terms for coagulation "acceleration" and "deceleration"; and 4) the magnitude of signal change during coagulation. FIG. 1 shows a typical optical profile based on transmittance and the associated derivatives. The parameters are defined in FIG. 2.

After defining the set of predictor variables, a model (113) is derived which represents the set of predictor variables from the known populations of specimens. This model can be derived from a topological feature map in one embodiment of the present invention. In another embodiment, the model is derived via a set of statistical equations.

After deriving the model (113), whether based on topological feature maps or statistical equations, the model is utilized to present (120) the unknown sample's relationship to the known population(s). The user may then interpret these relationships and perform confirming assays (121). The output of the model (120) can be automatically stored in a memory (122) of an automated analyzer and/or displayed relative to one or more known sample populations (124) on the automated analyzer, such as on a computer monitor, or printed out on paper. Also, where the unknown sample is from a medical patient, both the derived model and other patient medical data (95) can be used for generating a model and subsequent relationship to it.

EXAMPLE

Presentation of Data Using Topological Feature Maps

This example demonstrates how data from known sample populations can be used to generate a topological feature map that can then be used to present the relationships between an unknown sample and known sample populations for analysis.

Self-organizing feature maps were used to generate the topological feature maps. A self-organizing feature map is a type of neural network that includes an input and output layer of neurons. The network is trained by a competitive learning algorithm where the output neurons compete with one another to be activated and only one output neuron is activated for any given set of inputs. Once trained, the self-organizing map (SOM) algorithm transforms an input vector to an individual output neuron whose location in the output layer, or map, corresponds to features of the input data. These features tend to be spatially correlated in the map. In this example, the presentation of the data from the known specimens was generated in the following steps:

1. PT and APTT assays were performed on an automated analyzer for 765 samples. These samples represented 200 patient specimens that included normal patients, patients with a variety of deficiencies, and patients undergoing heparin or oral anticoagulant therapy.
2. The 200 specimens were also tested to determine the concentration of coagulation factors (FII, FV, FVII, FVIII, FIX, FX, FXI, FXII) heparin, and fibrinogen.

3. Time-dependent optical measurements were taken and the data profiles stored for all PT and APTT assays performed in step 1.
4. The nine predictor variables defined in FIG. 2 were calculated for all profiles stored in step 3.
5. A 10×10 SOM was trained using the 765 sets of nine PT predictor variables from step 4.
6. A 10×10 SOM was trained using the 765 sets of nine APTT predictor variables from step 4.
7. Contour plots were constructed for six categories of known specimen classifications: normal donors, specimens with heparin >0.05 IU/ml, fibrinogen >600 mg/dl, fibrinogen <200 mg/dl, patients receiving oral anticoagulants, and factor-deficient specimens (specimens with <30% of normal activity for FII, FV, FVII, FVIII, FIX, FX, FXI, or FXII). These contour plots depict the distribution of specimens within a category according to their map coordinates. The shaded areas represent the distribution of output neurons for specific specimen populations within the feature map. Each contour line represents an incremental step of one test result located at a given set of map coordinates.

Figure 3:
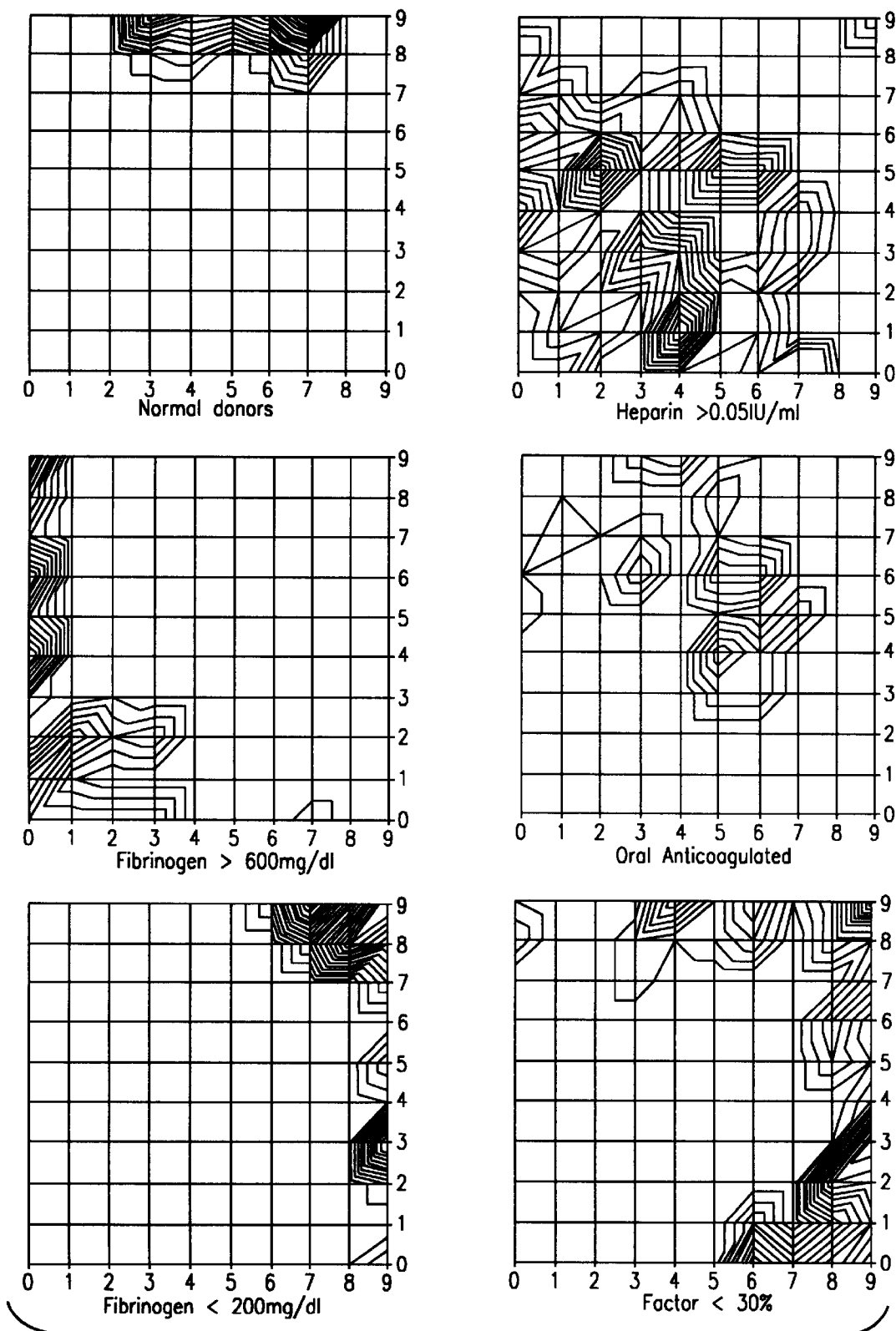
FIG. 3 shows self-organizing map (SOM) contour plots derived from APTT optical data for six specimen categories.

FIG. 3 shows SOM contour plots derived from APTT optical data. Specimens containing low fibrinogen and high fibrinogen were classified at opposite borders of the SOM with no overlap. Normal populations showed some overlapping with low fibrinogen, factor deficient and oral anticoagulated categories. Overlap between normal specimens and edges of the high and low fibrinogen populations is expected, since some proportion of healthy donors have fibrinogen levels that are lower or higher than normal. Overlap between mapping of normal specimens and factor-deficient plasmas is also not surprising, since APTT tests are sensitive to some factor-deficiencies (but not others), whereas PT assays are sensitive to a separate subset of factor deficiencies. The low fibrinogen category tended to overlap the factor-deficient category, consistent with our observation that many factor-deficient specimens also had reduced fibrinogen levels. The heparin category tended to overlap the high fibrinogen category, again consistent with measured levels of fibrinogen for these specimens. Little or no overlap was observed between normal specimens and specimens containing heparin. Specimens from patients receiving oral anticoagulant therapy show significant overlap with both normal and heparin populations. This is consistent with known properties of APTT assays, which are sensitive to heparin therapy but relatively insensitive to oral anticoagulant therapy.

Contour plots for self-organizing feature maps trained with PT data are shown in FIG. 4. Results are similar to maps from APTT data in several respects: (1) high and low fibrinogen were well resolved at opposite sides of the map; (2) normal specimens were localized in a region that overlapped low fibrinogen specimens slightly; (3) factor-deficient specimens were distributed between non-overlapping regions and regions that overlapped low fibrinogen and normal populations. Overlap was consistent with measured fibrinogen for some specimens, and with poor sensitivity of PT reagents to some factor deficiencies in other cases; (4) oral anticoagulated specimens showed some overlap with both normal and heparin populations; and (5) the heparinized population was distributed over a large portion of the map. Overlap between heparinized specimens and high fibrinogen populations was consistent with measured fibrinogen levels.

These results indicate that self-organizing feature maps are capable of distinguishing differences in optical data parameters from APTT and PT assays even when no information regarding specimen diagnosis is presented to the neural network. Resolution of specimen populations was variable, depending on reagent properties and sensitivities, and on whether specimens belonged to a given category uniquely or to multiple overlapping categories.

To present the data from an unknown sample, the following additional steps would be taken:
1. Perform a PT and/or APTT assay on the unknown sample.
2. Collect the time-dependent optical data from the assay and store it.
3. Calculate the parameters that comprise the input vector of the trained SOM.
4. Determine the winning output neuron for that particular set of inputs.
5. Display the position of the unknown sample on the contour plots generated in the first part of this example.

EXAMPLE

Presentation of Data using a Statistical Model

This example demonstrates how data from known sample populations can be used to generate statistical descriptions which can then be used to present the relationships between an unknown sample and known sample populations for analysis.

The following steps were performed for PT assays (see FIG. 5) and then separately for APTT assays (see FIG. 6):
1. Mean and standard deviation (SD) were calculated for each of the nine parameters described in FIG. 2 from assays (PT or APTT) run on aliquots from normal specimens (n=79).
2. Z-scores were calculated for each parameter of each specimen from the normal group (n=79) and abnormal group (n=410). Z-scores are calculated by subtracting the mean of normals from the clot time and then dividing the result by the SD. The group of abnormals included various factor deficiencies, oral-anticoagulated specimens, suspected disseminated intravascular coagulation (DIC) specimens, and heparinized specimens.
3. Classifying normal samples as negative and all abnormals as positive, the number of true positives, true negatives, false positives and false negatives were determined. If specimens with an absolute value of the z-score greater than x SD (where x=1,2,3,4,5, etc.) for one or more of the parameters, the specimen was called positive.
4. For comparison, steps 1 through 3 were repeated for PT and APTT clot times.

Sensitivity and specificity for non-specific abnormals as a group is higher when using all parameters rather than the traditional clot time used alone.

Many additional and alternate features are envisioned as being encompassed within the scope of the present invention. For example, the known blood samples could be samples of which information is known relating to one or more intrinsic or extrinsic clotting factors and/or therapeutic agents, or are normal samples. Also, in addition to the predictor variables mentioned above, additional patient medical data associated with each sample can be used as the input vector for the map. Further, a plurality of coagulation assays can be performed to provide the time-dependent measurement profile, and a plurality of optical measurements can be made over time at multiple wavelengths for one or more of the time-dependent measurement profiles. And, the resultant feature maps can be displayed on any suitable display, such as a computer monitor, paper printout, etc.

It is to be understood that the invention described and illustrated herein is to be taken as a preferred example of the same, and that various changes in the method and apparatus of the invention may be resorted to, without departing from the spirit of the invention or scope of the claims.

We claim:

1. A method for presenting the relationship between data from an assay relating to thrombosis-hemostasis on an unknown sample, and data from a plurality of assays relating to thrombosis-hemostasis from known sample populations comprising:

(a) providing data from at least one time-dependent measurement for each of a purality of known blood samples;

(b) measuring a property over time to derive at least one time-dependent measurement on an unknown blood sample;

(c) transforming data from steps (a) and (b) to at least one predictor variable which captures information content of both the unknown blood sample's at least one time-dependent measurement and the at least one time-dependent measurement for each of said plurality of known blood samples;

(d) creating a topological feature map of the at least one predictor variable from step (c) of the plurality of known blood samples in step (a) whose spatial locations within the topological feature map correspond to intrinsic features of the at least one predictor variable;

(e) determining the position on the topological feature map of the unknown blood sample corresponding to the unknown blood sample's at least one predictor variable; and (f) presenting the position of the unknown blood sample and the positions of the plurality of known samples used to create the map in step (d) on the map created in step (d).

2. The method according to claim 1, wherein in step (c), data from the at least one time-dependent measurement in steps (a) and (b) is transformed into at least one predictor variable that characterizes timing, rate and/or magnitude of changes over time during the at least one time-dependent measurement of steps (a) and (b).

3. The method according to claim 2, wherein said at least one predictor variable in step (c) includes a minimum of the first derivative of the at least one time-dependent measurement.

4. The method according to claim 2, wherein said at least one predictor variable in step (c) includes a time index of the minimum of the first derivative of the at least one time-dependent measurement.

5. The method according to claim 2, wherein said at least one predictor variable in step (c) includes a minimum of the second derivative of the at least one time-dependent measurement.

6. The method according to claim 2, wherein said at least one predictor variable in step (c) includes a time index of the minimum of the second derivative of the at least one time-dependent measurement.

7. The method according to claim 2, wherein said at least one predictor variable in step (c) includes a maximum of the second derivative of the at least one time-dependent measurement.

8. The method according to claim 2, wherein said at least one predictor variable in step (c) includes a time index of the maximum of the second derivative of the at least one time-dependent measurement.

9. The method according to claim 2, wherein said at least one predictor variable in step (c) includes an overall change in the at least one time-dependent measurement.

10. The method according to claim 2, wherein said at least one predictor variable in step (c) includes a clotting time.

11. The method according to claim 2, wherein said at least one predictor variable in step (c) includes a slope of the at least one time-dependent measurement prior to clot formation.

12. The method according to claim 2, wherein said at least one predictor variable in step (c) includes a slope of the at least one time-dependent measurement after clot formation.

13. The method according to claim 1, wherein said plurality of known blood samples and said unknown blood samples are samples of whole blood or plasma.

14. The method according to claim 1, wherein said plurality of known blood samples are samples of which information is known relating to one or more intrinsic or extrinsic clotting factors and/or therapeutic agents, or are normal samples.

15. The method according to claim 1, wherein said at least one time-dependent measurement comprises at least one time-dependent measurement from a prothrombin time assay.

16. The method according to claim 1, wherein said at least one time-dependent measurement comprises at least one time-dependent measurement from an activated partial thromboplastin time assay.

17. The method according to claim 1, wherein at least one of said at least one time-dependent measurement consists of an optical measurement.

18. The method according to claim 17, wherein said optical measurement correspond to changes in light scattering and/or light absorption.

19. A method according to claim 1, wherein in addition to the at least one predictor variable in step (c), additional patient medical data associated with each blood sample is used for creating the topological feature map.

20. The method according to claim 1, wherein in steps (a) and (b), a plurality of assays relating to thrombosis-hemostasis are performed to provide said at least one time-dependent measurement of step (a) and (b).

21. The method according to claim 1, wherein a plurality of topological feature maps are provided for presenting data in step (f).

22. A method according to claim 1, wherein said at least one time-dependent measurement in steps (a) and (b) is provided by an automated analyzer for thrombosis and hemostasis testing.

23. A method according to claim 22, wherein a plurality of optical measurements are made at multiple wavelengths.

24. A method according to claim 22, wherein at least one time-dependent measurement is provided automatically by said automated analyzer, and the unknown blood sample is automatically removed by an automated probe from a sample container to a test well, one or more reagents are automatically added to the test well to initiate property changes over time within said blood sample, and the development of changes over time is automatically monitored to derive a time-dependent measurement.

25. A method according to claim 22, wherein after step (e), the position of the unknown blood sample on the map is stored in a memory of said automated analyzer and/or displayed on said automated analyzer.

26. A method for presenting the relationship between data from an assay relating to thrombosis-hemostasis on an unknown sample, and data from a plurality of assays relating to thrombosis-hemostasis from known sample populations comprising:

(a) providing data from at least one time-dependent measurement for each of a plurality of known blood samples;

(b) measuring a respective property over time to derive data comprising at least one time-dependent measurement on an unknown blood sample;

(c) transforming data from steps (a) and (b) to at least one predictor variable which captures information content of both the unknown blood sample's at least one time-dependent measurement and the at least one time-dependent measurement for each of said plurality of known blood samples;

(d) computing the standard deviation for each predictor variable in step (c) of the plurality of known blood samples in step (a)

(e) determining the z-score of the unknown blood sample in (b) for each predictor variable, and determining if one or more of the z-scores for the unknown blood sample is greater than a predetermined limit, signifying that the unknown blood sample is different from the plurality of known blood samples represented by the at least one predictor variable.

27. The method according to claim 26, wherein in step (c), data from the at least one time-dependent measurement in steps (a) and (b) is transformed into at least one predictor variable that characterizes timing, rate and/or magnitude of changes during the at least one time-dependent measurement in steps (a) and (b).

28. The method according to claim 27, wherein said at least one predictor variable in step (c) includes a minimum of the first derivative of the at least one time-dependent measurement.

29. The method according to claim 27, wherein said at least one predictor variable in step (c) includes a time index of the minimum of the first derivative of the at least one time-dependent measurement.

30. The method according to claim 27, wherein said at least one predictor variable in step (c) includes a minimum of the second derivative of the at least one time-dependent measurement.

31. The method according to claim 27, wherein said at least one predictor variable in step (c) includes a time index of the minimum of the second derivative of the at least one time-dependent measurement.

32. The method according to claim 27, wherein said at least one predictor variable in step (c) includes a maximum of the second derivative of the at least one time-dependent measurement.

33. The method according to claim 27, wherein said at least one predictor variable in step (c) includes a time index of the maximum of the second derivative of the at least one time-dependent measurement.

34. The method according to claim 27, wherein said at least one predictor variable in step (c) includes an overall change in the at least one time-dependent measurement.

35. The method according to claim 27, wherein said at least one predictor variable in step (c) includes a clotting time.

36. The method according to claim 27, wherein said at least one predictor variable in step (c) includes a slope of the at least one time-dependent measurement prior to clot formation.

37. The method according to claim 27, wherein said at least one predictor variable in step (c) includes a slope of the at least one time-dependent measurement after clot formation.

38. The method according to claim 26, wherein said plurality of known blood samples and said unknown blood sample are samples of whole blood or plasma.

39. The method according to claim 26, wherein said plurality of known blood samples are samples of which information is known relating to one or more intrinsic or extrinsic clotting factors and/or therapeutic agents, or are normal samples.

40. The method according to claim 26, wherein said at least one time-dependent measurement comprises at least one time-dependent measurement from a prothrombin time assay.

41. The method according to claim 26, wherein said at least one time-dependent measurement comprises at least one time-dependent measurement from an activated partial thromboplastin time assay.

42. The method according to claim 26, wherein at least one of said at least one time-dependent measurement comprises an optical measurement.

43. The method according to claim 42, wherein said optical measurement corresponds to changes in light scattering and/or light absorption.

44. The method according to claim 26, wherein in steps (a) or (b), a plurality of assays relating to thrombosis-hemostasis are performed to provide said at least one time-dependent measurement.

45. A method according to claim 26, wherein said at least one time-dependent measurement in steps (a) and (b) is provided by an automated analyzer for thrombosis and hemostasis testing.

46. A method according to claim 45, wherein at least one time-dependent measurement is provided automatically by said automated analyzer, and the unknown blood sample is automatically removed by an automated probe from a sample container to a test well, one or more reagents are automatically added to said test well so as to initiate property changes over time within said blood sample, and the development of respective property changes over time is automatically monitored so as to derive a data profile.

47. A method according to claim 45, wherein after step (e), the z-scores of the unknown blood sample are stored in a memory of said automated analyzer and/or displayed on said automated analyzer.

48. A method according to claim 26, wherein a plurality of optical measurements are made at multiple wavelengths.

* * * * *